United States Patent [19]

Rosenmeier et al.

[11] Patent Number: 5,789,106
[45] Date of Patent: Aug. 4, 1998

[54] ION-CONDUCTIVE POLYMERS

[75] Inventors: Lars Rosenmeier, Vedbæk; Boye Cornils Knutz, Copenhagen, both of Denmark

[73] Assignee: Danacell ApS, Denmark

[21] Appl. No.: 849,090

[22] PCT Filed: Nov. 30, 1995

[86] PCT No.: PCT/DK95/00484

§ 371 Date: Jul. 22, 1997

§ 102(e) Date: Jul. 22, 1997

[87] PCT Pub. No.: WO96/17359

PCT Pub. Date: Jun. 6, 1996

[30] Foreign Application Priority Data

Dec. 1, 1994 [DK] Denmark .................. 1370/94

[51] Int. Cl.[6] .................................................. H01M 10/40
[52] U.S. Cl. .................. 429/192; 252/62.2; 429/33
[58] Field of Search ...................... 429/192, 33, 30;
252/62.2; 525/314; 359/270

[56] References Cited

U.S. PATENT DOCUMENTS

| 5,196,484 | 3/1993 | Giles et al. | |
| 5,350,646 | 9/1994 | Armand et al. | |
| 5,665,265 | 9/1997 | Gies et al. | 252/62.2 |
| 5,681,357 | 10/1997 | Eschbach | 29/623.5 |

FOREIGN PATENT DOCUMENTS

| 0420253A2 | 4/1991 | European Pat. Off. |
| 0421546A2 | 4/1991 | European Pat. Off. |
| 0460876A1 | 12/1991 | European Pat. Off. |
| 0581296A2 | 2/1994 | European Pat. Off. |

OTHER PUBLICATIONS

Patent Abstracts of Japan, vol. 15, No. 70, E–1035, Abstract of Japan, A, 2–291603 (Hitachi Maxell Ltd), 3 Dec. 1990.

*Primary Examiner*—M. Nuzzolillo
*Attorney, Agent, or Firm*—Birch, Stewart, Kolasch & Birch, LLP

[57] ABSTRACT

Ion-conductive polymers with high ion conductivity and containing covalently bound ion complexes of one of formulas (IA–IC), wherein $M^+$ is $H^+$, $Li^+$, $Na^+$, or $K^+$; m is an integer in the range 0–4; m' is an integer in the rage 0–7; m" is an integer in the range 0–8; and each R independently is halogen; $-CO-O^-$, $-CO-O^-$, $M^+$, or $-SO_2-O^-$, $M^+$; cyano; nitro; $C_{1-5}$ alkoxy; optionally substituted phenyl or phenoxy; $-CONR^5R^6$ or $-NR^5R^6$ where $R^5$ and $R^6$ independently are hydrogen, $C_{1-5}$ alkyl, optionally substituted phenyl, phenylcarbonyl, or $C_{1-6}$ alkanoyl; $-N(R^6)-CO-R^7$ where $R^7$ is hydrogen, $C_{1-5}$ alkyl, $C_{2-5}$ alkenyl, $C_{2-5}$ alkynyl, or optionally substituted phenyl; $R^7-CO-$, $R^7-O-CO-$, or $R^7-O-CO-O-$; cycloheptatrienyl; or one of the groups R is an ion complex of the type Ia, Ib, or Ic with the proviso that R cannot be a further ion complex of the type Ia, Ib, or Ic; or two groups R bound to two adjacent carbon together form a divalent aliphatic or alicyclic group with 3–8 carbon atoms and having at least 2 C—C double bonds, $-CO-O-CO-$, $-CO-S-CO-$, or $-CO-N(R^7)-CO-$; and the free bond "a" either directly or through an intervening group, is bound to the polymer backbone.

20 Claims, No Drawings

ION-CONDUCTIVE POLYMERS

FIELD OF THE INVENTION

The present invention concerns ion-conductive polymers which are useful as electrolytes in electrochemical devices such as rechargeable batteries and fuel cells.

BACKGROUND OF THE INVENTION

The production, storage, and distribution of energy are among the main concerns of modern industry and society. Thus, the efficient exploitation of energy sources that generate electricity on an intermittent basis, e.g. solar energy, wind and wave power, require the availability of low-cost, high-efficiency electricity storage systems. Similarly, the increasingly widespread use of various portable electronic devices and appliances having fairly high power requirements, such as mobile telephones, portable music and video systems (compact cassette recorders/players, CD-players, video camcorders etc.), laptop computers and the like, has increased the number of rechargeable battery units in use by a significant factor. Finally, the desire to reduce urban air pollution has resulted in the development of electric automobile systems that have highlighted the shortcomings of existing battery systems with respect to price, power-to-weight ratio, and/or environmental concerns due to use of environmentally problematic materials such as heavy metals.

There have been a number of attempts at using ion-conductive polymers as electrolytes in batteries, i.a. in connection with the use of alkali metals as electrode material combined with the corresponding alkali metal cation as the charge carrier through the electrolyte. Lithium in particular is attractive for high-density batteries due to its low specific density, high standard potential and high melting point. Such attempts include the use of alkali metal salts such as $LiClO_4$ solvated in a poly(alkylene oxide) matrix and the use of covalently bound ion-polymer complexes such as phenolate derivatives covalently bound to a poly(methyl hydrosiloxane) backbone.

In the case of solvated salt, the stability of the alkali metal electrode is believed to depend on the formation of a passivation layer which is due to an irreversible chemical reaction between the counter anion and the alkali metal electrode. However, despite relatively high ion conductivities of such electrolytes, the passivation phenomenon seriously limits the lifetime of the battery.

The passivation problem may be solved partially by covalently binding the anions to the backbone as has been done with the use of phenolates. However, although the anions are immobilized on the polymer matrix, these attempts have not resulted in electrolytes with ion conductivities of practically useful magnitude due to low dissociation constant of the lithium/phenolate ion pair and/or to the use of systems of inferior ion-solvating properties.

Consequently, there is a need for ion-conductive polymers that are stable in contact with the electrode materials and have ion conductivities of a magnitude that makes them practically applicable as electrolytes for inclusion into batteries or fuel cells.

SUMMARY OF THE INVENTION

It has now been found that surprisingly high ion conductivities can be obtained by means of polymers containing ion complexes comprising covalently bound carbocyclic anionic groups, the anion groups being aromatic and having been rendered aromatic as a result of the anion formation through the removal of at least one $H^+$ ion. The aromatic, carbocyclic anionic groups may be substituted by various groups including electron-withdrawing groups.

In particular, the invention concerns an ion-conductive polymer containing covalently bound ion complexes of one of the formulas Ia–Ic

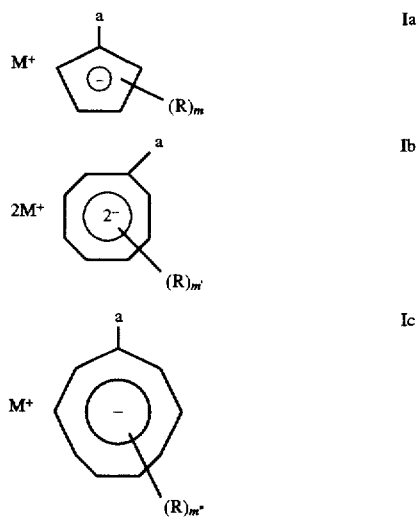

wherein
$M^+$ is $H^+$, $Li^+$, $Na^+$, or $K^+$;
m is an integer in the range 0–4;
m' is an integer in the range 0–7;
m" is an integer in the range 0–8; and
each group R independently is
  halogen;
  a group —CO—O⁻, —CO—O⁻.$M^+$, or —SO₂—O⁻, $M^+$ wherein $M^+$ is as defined above;
  cyano;
  nitro;
  $C_{1-5}$ alkoxy;
  optionally substituted phenyl;
  optionally substituted phenoxy;
  a group —CONR⁵R⁶ where R⁵ and R⁶ independently are hydrogen, $C_{1-5}$ alkyl, optionally substituted phenyl, phenylcarbonyl, or $C_{1-6}$ alkanoyl;
  a group —NR⁵R⁶ where R⁵ and R⁶ independently are as defined above;
  a group —N(R⁵)—CO—R⁷ where R⁵ is as defined above, and R⁷ is hydrogen, $C_{1-5}$ alkyl, $C_{2-5}$ alkenyl, $C_{2-5}$ alkynyl, or optionally substituted phenyl;
a group R⁷—CO—, a group R⁷—O—CO—, a group R⁷—CO—O—, or a group R⁷—O—CO—O— where R⁷ is as defined above; cycloheptatrienyl; or
one of the groups R is a ion complex Ia', Ib', or Ic'

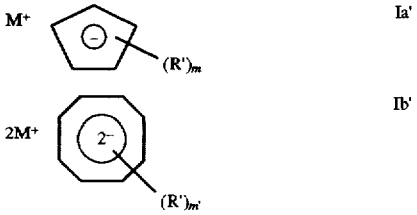

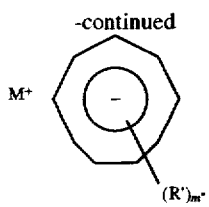

wherein M⁺, m, m' and m" are as defined above, and R' has the same meanings as R defined above with the proviso that R' is not a ion complex Ia', Ib', or Ic';

or two groups R bound to two adjacent carbon atoms may together form a divalent aliphatic or alicyclic group with 3–8 carbon atoms and having at least 2 C—C double bonds; carbonyloxycarbonyl;

carbonylthiocarbonyl; or a group —CO—N(R⁷)—CO— where R⁷ is as defined above;

and the free bond indicated by "a", either directly or through an intervening group, is bound to the polymer backbone.

DETAILED DESCRIPTION OF THE INVENTION

In the present context, the term "$C_{1-5}$ alkyl" designates an alkyl moiety of 1–5 carbon atoms such as methyl, ethyl, n-propyl, isopropyl, n-butyl, isobutyl, sec-butyl, tert-butyl, n-pentyl, or neopentyl. The term "$C_{2-5}$ alkenyl" designates a monounsaturated hydrocarbyl group with 2–5 carbon atoms, such as vinyl, allyl, 1-, 2-, or 3-propenyl, n-butenyl, sec-butenyl, iso-butenyl, n-pentenyl, sec-pentenyl, iso-pentenyl. The term "$C_{2-5}$ alkynyl" designates a hydrocarbyl group with 2–5 carbon atoms and containing a triple bond, such as ethynyl, propynyl, n-butynyl, sec-butynyl, iso-butynyl, n-pentynyl, iso-pentynyl. The term "$C_{1-5}$ alkoxy" designates a $C_{1-5}$ alkyl group as defined bound via an oxygen atom. The term "$C_{1-6}$ alkanoyl" designates the acyl group derived from an alkanoic acid with 1–6 carbon atoms, such as formyl, acetyl, propionyl, butyryl, valeryl or hexanoyl.

The term "halogen" designates fluoro, chloro, bromo, and iodo.

The terms "optionally substituted phenyl" and "optionally substituted phenoxy" designate phenyl and phenoxy groups, respectively, which are unsubstituted or are substituted with, electron-withdrawing groups such as halogen, cyano, nitro, $C_{1-5}$ alkoxy, a group —CONR⁵R⁶ as defined above, a group —NR⁵R⁶, as defined above, a group —N(R⁵)—CO—R⁷ as defined above, a group R⁷—CO— as defined above, a group R⁷—O—CO— as defined above, a group R⁷—CO—O— as defined above, or a group R⁷—O—CO—O— as defined above.

When two groups R bound are to two adjacent carbon atoms and together form a divalent aliphatic or alicyclic group, examples of such divalent groups are 1,3-propenylene, 1- or 2-buten-1,4-ylene, 1,3-butadien-1,4-ylene, 1,3-pentadien-1,5-ylene, 5-methyl-1,3-pentadien-1,5-ylene, 3-methyl-1,4-pentadien-1,5-ylene, 5-methylidene-1,3-pentadien-1,5-ylene, a group of the formula

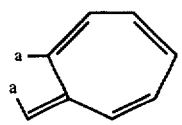

and a group of the formula

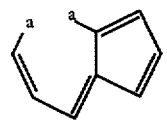

where "a" indicates the free bonds.

Specific, but not limiting examples of covalently bound ion complexes of the formulas Ia–Ic wherein two groups R bound to adjacent carbon atoms form the above defined groups are as follows:

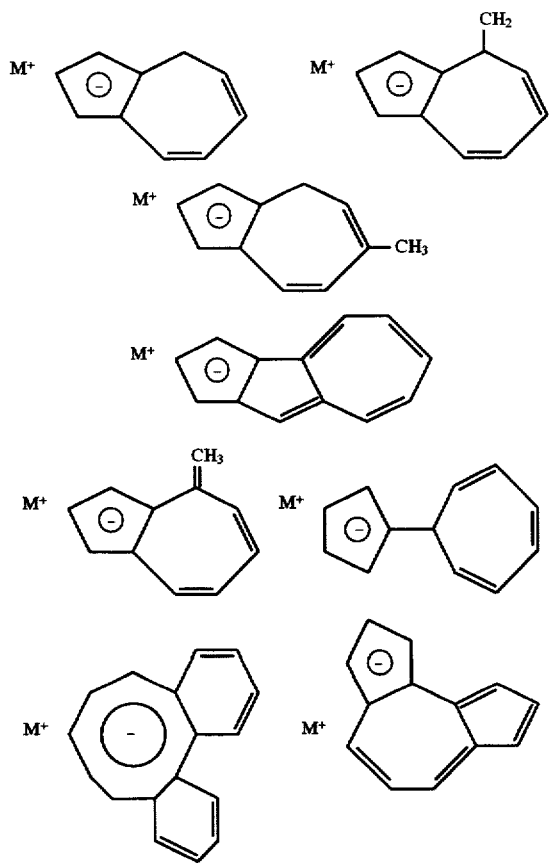

where the free bond "a" shown in the formulas Ia–Ic may be in any of the possible positions.

It is particularly preferred if the divalent group together with the cyclic nucleus in the formulas Ia–Ic forms a complete aromatic structure.

Preferred examples of the covalently bound anion in the ion complexes of the formulas Ia–Ic are the cyclopentadienylide ion, the indenylide ion, and the 9-fluorenylide ion, in particular the cyclopentadienylide ion.

Since the ion conductivity of an ion conductive polymer is unfavourably affected at temperatures below the glass transition temperature of the polymer due to crystallization of the ion-solvating polymer matrix, it is preferred that the glass transition temperature $T_g$ of the polymer of the invention is below 273° K, more preferably below 263°0K, most preferably below 253° K, in particular below 243° K, especially below 233° K, such as below 223° K.

It has been established that a prerequisite for ion-conductivity is the presence of a suitably ion-solvating environment capable of solvating the ions, and in order to ensure such an environment, an ion solvating solvent may be incorporated into the electrolyte, e.g. tetrahydrofuran or propylene carbonate.

However, it is known that the ion conductivity is also improved in the presence of poly(alkylene oxide) moieties in the polymer, and it is therefore preferred that such moieties are present in the polymer. It is particularly preferred that the polymer of the invention comprises sequences of the formula —(CH(Y)—CH$_2$—O)$_n$— where Y is hydrogen or methyl, and n is an integer in the range of 2–30 depending on the polymeric system selected, in particular in the range 3–10. Such sequences may be present either in the backbone of the polymer or in grafted side groups or in the intervening group. It has been shown that poly(alkylene oxide)s form canal-like structures in the polymeric matrix with the right dimensions for ion passage through the electrolyte.

Depending on the precise composition of the poly(alkylene oxide) moieties in the polymer, they may affect the $T_g$ of the polymer due to the formation of crystalline domains amongst the poly(alkylene oxide) moieties present. While it has been found that such effects can be off-set by forming the electrolyte from a mixture of a polymer of the invention with for example polyisobutylene, it is also contemplated that the effect may be eliminated or substantially reduced by omitting forming the poly(alkylene oxide) moieties from identical units, thereby introducing an element of heterogeneity in the poly(alkylene oxide) moieties.

Since it is chiefly the properties of the ion complexes of the formulas Ia–Ic which are responsible for the surprising ion conductivity properties of the polymers of the invention, the backbone in the polymers may in principle be any type of polymer which does not actually contain functionalities which would directly counteract the intended ion transport process such as groups or functionalities capable of binding strongly with $M^+$.

Examples, although by no means exhaustive, of general types of polymers which may form the basis for at least part of the backbone of the polymers of the invention are derivatives of polyolefines such as polyethylene, polypropylene or polyisobutylene; polymers of unsaturated acids such as acrylic acid, methacrylic acid, itaconic acid as well as derivatives of such acids such as esters, nitriles or amides, e.g. polyacrylic acid, poly(polyethoxymethylitaconate) (PEO(n)MI), poly(polyethyleneglycol methacrylate) (PGM), poly(hydroxyethyl acrylate); polyvinyl alcohol and derivatives thereof such as polyvinyl esters, e.g. polyvinyl acetate; derivatives of polyesters, typically formed from a diacid (e.g. adipic acid, terephthalic acid) and a dihydroxy compound (e.g. ethylene glycol, propylene glycol), such as poly(ethylene adipate); derivatives of polyamides, typically formed from a diacid (e.g. adipic acid, terephthalic acid) and a diamino compound (e.g. 1,3-diaminopropane, 1,4-diaminobutane, 1,6-diaminohexane); polyalkyleneimines, both linear and branched, such as polyethyleneimine; substituted polyphosphazenes such as poly(bis-(methoxyethoxy-ethoxide)phosphazene; silicone polymer derivatives such as polysiloxane derivatives, e.g. derivatives of poly(methylhydrosiloxane).

Furthermore, the polymer may be either crosslinked or non-crosslinked, and the crosslinking may have been brought about in any manner known in the art, e.g. through reaction of reactive groups on the backbone or a grafted side group thereon with crosslinking moieties having two or more functionalities; or through irradiation with ultraviolet light (optionally in the presence of UV-sensitive initiators such as benzophenone or benzoylperoxide), X-rays, gamma rays or electron beams (EB).

The term "intervening group" is intended to mean any chemical moiety located between on the one hand the ion complexes of the formulas Ia–Ic defined above and on the other hand the polymer backbone. Since, as discussed above, it is the properties of the ion complexes of the formulas Ia–Ic which are chiefly responsible for ion conductivity properties of the polymers, it is clear that similar to the polymer backbone, the intervening group may in principle be any type of divalent chemical group or moiety which does not actually contain functionalities which would directly counteract the intended ion transport process.

As examples, but by no means exhaustive, of intervening groups may be mentioned the following where the lefthand end of the various formulas is connected to the polymer backbone, and the righthand end is connected to the ion complex of the formulas Ia–Ic:

—(CH$_2$)$_x$— where x is an integer from 1 to 10;

—(CH$_2$)$_{x'}$-(Phenyl)-, where x' is an integer from 1 to 10;

—O—;

—O-(Phenyl)-;

—O—(CH$_2$)$_{x''}$—, where x" is an integer from 1 to 10;

—O—(CH$_2$)$_{x'}$-(Phenyl)-, where x' is as defined above; and

—(CH$_2$)$_y$—O—CH$_2$—CH(OH)—CH$_2$—, where y is an integer from 1 to 10.

In the above formulas, the group (Phenyl) designates a benzene ring, the substitution pattern of which may be 1,2-, 1,3-, or 1,4-, and the remaining positions on the ring are unsubstituted or may be substituted with any group capable of delocalizing the charge of the anion, e.g. cyano; nitro; $C_{1-5}$ alkoxy; optionally substituted phenyl; optionally substituted phenoxy; a group —CONR$^5$R$^6$ where R$^5$ and R$^6$ independently are hydrogen, $C_{1-5}$ alkyl, optionally substituted phenyl, phenylcarbonyl, or $C_{1-6}$ alkanoyl; a group —NR$^5$R$^6$ where R$^5$ and R$^6$ independently are as defined above; a group —N(R$^5$)—CO—R$^7$ where R$^5$ is as defined above, and R$^7$ is hydrogen, $C_{1-5}$ alkyl, $C_{2-5}$ alkenyl, $C_{2-5}$ alkynyl, or optionally substituted phenyl; a group R$^7$—CO—, a group R$^7$—O—CO—, a group R$^7$—CO—O—, or a group R$^7$—O—CO—O— where R$^7$ is as defined above.

In another embodiment of the polymer, sequences of the formula —(CH(Y)—CH$_2$—O)$_n$— discussed above are comprised in the intervening groups between the ion complexes of the formulas Ia–Ic and the polymer backbone.

The backbone of the polymer may be one which is derived from one of the following examples of polymers which, however, should not be construed as being limiting. In the examples, the basic structure of the polymer is given by showing the repeating units, but without showing where the location of the ion complex group of the formula Ia–Ic or the group containing the ion complex group. Thus, the backbone may be derived from polymer backbones of the following formulas II, III or IV

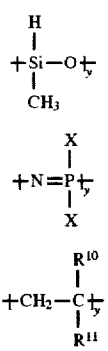

wherein X is halogen; $R^{10}$ and $R^{11}$ independently are hydrogen, alkyl with 1–3 carbon atoms, carboxy, carboxyalkyl with 1–3 carbon atoms, phenyl, a group —(OCH(Y)CH$_2$)$_n$OH or a group —(OCH(Y)CH$_2$)$_n$OR$^{12}$ wherein Y is H or methyl, n is an integer in the range 2–30 and $R^{12}$ is C$_{1-3}$ alkyl; and y is an integer in the range from 3 to $10^4$, preferably from 3 to $10^3$, such as from 3 to 500.

In the formula II, it will typically be in the position of the silicon-bound hydrogen that an intervening group or an ion complex or, alternatively, a grafted side group is inserted as a result of the reactivity of the hydrogen-silicon bond. Likewise, in the formula III it will typically be in the position of the halogen atom that an intervening group or an ion complex or, alternatively, a grafted side group is inserted as a result of the reactivity of the phosphorous-halogen bond. In the formula IV, it will typically be somewhere in $R^{10}$ and/or $R^{11}$ that an intervening group or an ion complex or, alternatively, a grafted side group is inserted.

The polymers of the invention may typically be prepared from suitably substituted monomers by known methods of polymerisation analogous to the manner in which the type of polymer, from which a polymer of the invention is derived, is usually prepared. However, in some cases such as poly(ethylene glycol) ethers and poly(methyl siloxane)s, it may be more practical to introduce the ion complex groups or moieties containing them or grafted side groups into already existing polymers having suitable functionalities in their structure. As an example of a type of reagent capable of introducing an intervening group or a grafted side groups may be mentioned poly(ethylene glycol) allyl methyl diether, the double bond of which is able to react with the polymethylhydrosiloxane of formula II replacing the hydrogen in a hydrosilylation reaction.

When preparing the polymers of the invention from suitably modified monomers, the actual polymerization is typically performed in the same manner as known polymerizations relevant for the polymer in question, including the use of catalysts, coinitiators, solvents, proton traps, etc., cf. standard works in the polymer field such as M. P. Stevens, "Polymer Chemistry", Oxford University Press, 1990. Also, when the polymer contains poly(alkylene oxide) moieties, it may be advantageous to add an antioxidant, such as a sterically hindered phenol derivative, at the end of the polymerization reaction in order to prevent polymer degradation.

Similarly, the monomers may be modified by standard organic chemical methods as exemplified by the following.

Thus, the monomers for preparation of poly(vinyl ether)s (PVE) where the ether functions are of the poly(alkylene oxide) type, in particular the poly(ethylene oxide) type, may be for example synthesized from a mixture of ethyl vinyl ether and an appropriate poly(ethylene glycol)-monomethyl ether in the presence of mercuric acetate as a catalyst while heating the mixture at reflux temperature[15,16]. Ethylene glycol allyl vinyl diether for preparing allylated PVE may be prepared from allyl alcohol and (2-chloroethyl) vinyl ether, in the presence of a strong base such as potassium hydroxide, optionally in the presence of an aprotic solvent such as dimethyl sulfoxide (DMSO) at elevated temperatures, typically between 75° C. and 85° C.[15].

Monomers which are esters of unsaturated acids with an alcohol, such as poly(alkylene oxide)s or phenols, are typically prepared by acid catalyzed esterification of the unsaturated acid, e.g. itaconic acid, with an appropriate poly(alkylene oxide) or derivative thereof such as a suitable poly(ethylene glycol) or poly(ethylene glycol)-monomethyl ether, or with an appropriate phenol, or with a mixture of these, in the presence of e.g. p-toluene sulfonic acid catalyst in a solvent such as toluene at reflux temperature[17,18,19,20].

When polymerizing the modified monomers, other unmodified, unsaturated co-monomers such as isobutylene or styrene may be included.

For the preparation of polymers of the poly(methyl siloxane) type shown above, a suitable starting material may be a poly(methyl hydrosiloxane) which may then be reacted with a poly(ethylene glycol) allyl methyl diether or with allyl glycid ether or with styrene or a mixture of these in the presence of platinum catalyst[2]. The poly(ethylene glycol) allyl methyl ether used as a starting material may be prepared by a reaction between allyl chloride and the sodium salt of an appropriate poly(ethylene glycol) monomethyl ether, optionally in an aprotic solvent such as tetrahydrofuran (THF) at temperatures between 40° C. and 70° C.[10]. Similarly, poly(ethylene glycol) monomethyl ether and phenols can be grafted on to poly(methyl hydrosiloxane) in the presence of zinc octoate as a catalyst[2]. These reactions may be carried out at room temperature, optionally in an aprotic solvent such as THF. However, the use of zinc octoate requires the extraction thereof from the resulting polymer by a modified Soxhlet process.

A poly(alkylene oxide) matrix may also be introduced by mixing a polymer of the invention containing the ion complex of the formulas Ia–Ic (e.g. of the poly(methyl siloxane type) with 1) a copolymer of poly(ethylene glycol) methyl vinyl diether and ethylene glycol allyl vinyl diether; 2) poly(ethylene glycol)-crosslinked di-(poly(ethylene glycol) monomethyl ether)-polyphosphazene (DPP); or 3) poly (ethylene glycol)-crosslinked poly(di-poly(ethylene glycol) monomethyl ether) itaconate (PPI). Furthermore, any mixture of poly(ethylene glycol)-crosslinked DPP, poly (ethylene glycol)-crosslinked PPI and allylated PVE may serve the same purpose. In the case of allylated PVE, a crosslinking reaction occurs between the Si—H-bond in poly(methyl hydrosiloxane) and the double bonds in allylated PVE copolymer.

DPP, poly(ethylene glycol)-crosslinked DPP or phenylated DPP may be prepared by means of the ring-opening reaction of dichlorophosphazene at temperatures in the range 240°–260° C., followed by reaction with the sodium salt of poly(ethylene glycol) monomethyl ether, poly (ethylene glycol), phenol, or a mixture thereof in the presence of tetra-n-butyl ammonium bromide. The reactions may optionally be carried out in an aprotic solvent such as THF, at temperatures between 60° C. and 80° C.[7,8,9].

Polymers of the PVE-type, the polyalkene (such as polyisobutylene (PIB)) type, the polystyrene type, or combinations thereof may be prepared by carbocationic polymerization methods. The relevant starting materials are, in a typical example of such a polymerization reaction, reacted in a 40/60 (v/v) methylcyclohexane/dichloromethane solvent system with an initiating complex of titanium(IV)chloride and 1,3-di-(2-methoxy-2-propyl)-5-tert-butylbenzene in the presence of a proton trap such as 2,6-di-tert-butylpyridine, and in another typical example polymerized in dichloromethane with $BF_3Et_2O$ as the initiator at temperatures in the range from $-70°$ C. to $-90°$ C.[12,13,14,15,16].

Polymerization of unsaturated acid ester monomers such as itaconic acid diester monomers may be effected at temperatures in the range of $50°-60°$ C. using $\alpha,\alpha'$-azobisisobutyronitril as a radical initiator[17,18,19,20].

Polymers containing phenol- and/or styrene groups may furthermore be lithiated with alkyllithium (such as butyllithium (BuLi)) and then reacted with a suitable chemical compound for introducing a into the polymer precursor to the ion complex of the formulas Ia–Ic. One example of such a compound is 2-cyclopentene-1-on for introducing a cyclopentadienyl group onto the phenyl group. The ion complex is then formed by reacting the precursor group on the polymer with a metallating agent, for example an alkyllithium (such as methyllithium (MeLi) or BuLi) which then results in the formation of a lithium cyclopentadienylide group complex[3,4,5,6].

The ion-complex may also be introduced into the polymer either by adding a metal salt of the desired ion complex group to a polymer containing suitable functional groups with which to react; one example is the reaction between lithium cyclopentadienylide (LiCp) and an epoxy group on poly(methyl hydrosiloxane) carrying grafted allyl glycidyl ether groups.

Another aspect of the invention is a battery or a proton exchange membrane fuel cell comprising an electrolyte comprising a polymer of the invention. When a fuel cell is desired, a polymer in which $M^+$ is $H^+$ is used, whereas when $M^+$ is $Li^+$, $Na^+$, or $K^+$, the polymer is used in a battery. The polymers of the invention may also be used in other electrochemical devices such as electrochromic displays, "smart window" displays, electrochemical sensors, ion exchange matrixes (e.g. in desalination plants), galvanic cells, supercapacitors, and hydrogen concentration units.

A battery or a fuel cell according to the invention may be designed in a manner known per se to the person skilled in the art, e.g. as described in "Polymer Electrolyte Reviews" vol. 1 and 2, Ed. J. R. MacCallum & C. A. Vincent, Elsevier Applied Science, 1989; "Electrochemical Science and Technology of Polymers" vol. 2, Ed. R. G. Linford, Elsevier Applied Science, 1990; Fiona M. Gray, "Solid Polymer Electrolytes", VCH Publishers, 1991; and A. J. Appleby & F. R. Foulkes, "Fuel Cell Handbook", Van Nostrand, New York, 1989.

Thus, a typical example of a battery of the invention comprises a anode consisting of a sheet of nickel foil (serving as a current collector) laminated with a sheet of foil of the alkali metal in question, e.g. lithium foil with a thickness of 40–100 µm. The electrolyte is then laminated onto the alkali metal foil, the thickness of the polymeric electrolyte typically being the range 20–100 µm.

Finally, a cathode is laminated onto the surface of the electrolyte opposite the anode laminate. In order to be able to accommodate the alkali metal atoms resulting from the transport across the electrolyte of alkali metal ions, the cathode typically comprises a intercalating material, such as $TiS_2$, $V_2O_5$, $V_6O_{13}$, $MnO_2$, $CoO_2$, the alkali metal atoms resulting from the ion transport intercalating in vacant positions in the crystal lattice of the cathode material when the ion accepts an electron. In order to provide the cathode with sufficient electrical conductivity, the intercalation material is typically mixed with particles of an electrically conductive, but electrochemically inert material such as carbon, e.g. graphite and coke, and further contains a portion of the ion-conductive polymer.

The thickness of the entire laminate of anode, electrolyte, and cathode will depend on several factors but is typically up to a maximum of 2 mm. To provide batteries of cylindrical shape, the above laminate may simply be provided with suitable insulating layers and electrical connections and rolled or folded into the appropriate shape, e.g. a cylinder, and placed in a suitable casing.

A typical example of a proton exchange membrane fuel cell according to the invention comprises a pair of teflon-coated carbon gas diffusion electrodes laminated onto both sides of a membrane of a proton-conductive polymer according to the invention which has been platinized on both sides, i.e. has been coated with very small platinum particles (cf. M. S. Wilson & S. Gottesfeld, (Electronics Research Group, Los Alamos National Laboratory, USA), Thin-film Catalyst Layers for Polymer Electrolyte Fuel Cells, *Journal of Applied Electrochemistry*, 22 (1992) 1–7). The whole system is enclosed in a casing, and hydrogen or a hydrogen-containing gas (or methane) is supplied to the anode side of the membrane, while oxygen or an oxygen-containing gas is supplied to the cathode side of the membrane.

The manner in which the polymers of the invention are prepared as well as the procedures for producing single ion-conductive membranes containing an ion-polymer complex of the invention will be illustrated in more detail in the following, non-limiting examples.

All the reactions were carried out in dry, $O_2$-free solvents and under a dry, inert atmosphere ($N_2$ or Ar).

EXAMPLE 1

The synthesis of:

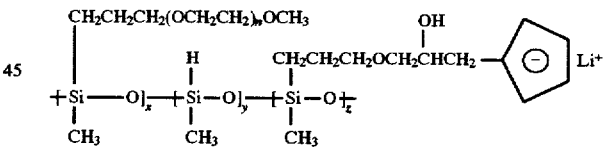

A tetrahydrofuran solution (40 ml) of polymethyl hydrosiloxane (1.18 g, $5.2.10^{-4}$ mole (PS 120)), polyethyleneglycol allyl methyl diether (2.12 g, $5.4.10^{-3}$ mole (MW=391)) and allyl glycidyl ether (0.45 g, $3.9.10^{-3}$ mole) was placed in a 50 ml Erlenmeyer flask. The reaction was catalyzed by adding 7.5 µl platinum-divinyltetramethyldisiloxan complex to the solution with a microsyringe[2]. The mixture was stirred for 72 hours followed by addition of lithium cyclopentadienylide (0.22 g, $3.0.10^{-3}$ mole, corresponding to a $EO/Li^+$ ratio of approximately 15. The solution was stirred for another 24 hours and cast on a glass plate. After the evaporation of the solvent the resulting polymer membrane (thickness approx. 0.25 mm) was dried at high vacuum. The conductivity of the complex was tested by means of a Solartron 1260 AC conductivity meter and was found to be $1.1.10^{-5}$ S $cm^{-1}$ at room temperature.

EXAMPLE 2

The synthesis of:

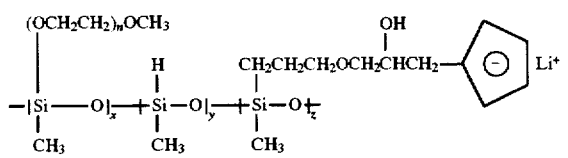

A tetrahydrofuran solution (40 ml) of polymethyl hydrosiloxane (1.25 g, 5.5.10$^{-4}$ mole (PS 120)) and polyethyleneglycol 350 monomethyl ether (2.20 g, 6.3.10$^{-3}$ mole) was placed in a 50 ml Erlenmeyer flask. The reaction was catalyzed by adding 25 mg of zinc octoate to the solution[2]. The mixture was stirred for 24 hours followed by addition of allyl glycidyl ether (0.39 g, 3.4.10$^{-3}$ mole) and 5 µl platinum divinyl tetramethyldisiloxan complex for catalyzing[2]. The mixture was stirred for 48 hours followed by addition of lithium cyclopentadienylide (0.16 g, 2.3.10$^{-3}$ mole), corresponding to a EO/Li$^+$ ratio of approximately 20. The solution was stirred for another 24 hours, filtered and then cast on a glass plate. After the evaporation of the solvent the resulting polymer membrane (thickness approx. 0.25 mm) was dried at high-vacuum. The conductivity of the complex was found to be 1.3.10$^{-5}$ S cm$^{-1}$ at room temperature.

EXAMPLE 3

The synthesis of:

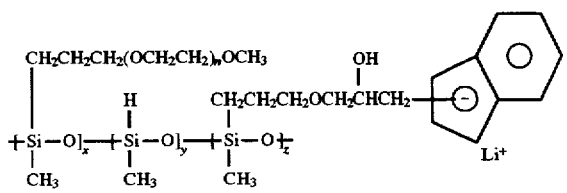

A tetrahydrofuran solution (40 ml) of polymethyl hydrosiloxane (1.38 g, 6.1.10$^{-4}$ mole (PS 120)), polyethyleneglycol allyl methyl diether (2.92 g, 7.5.10$^{-3}$ mole (MW=391)) and allyl glycidyl ether (0.37 g, 3.2.10$^{-3}$ mole) was placed in a 50 ml Erlenmeyer flask. The reaction was catalyzed by adding 7.5 µl platinum divinyl tetramethyldisiloxan complex to the solution with a microsyringe[2]. The mixture was stirred for 15 hours followed by addition of lithium indenylide (0.33 g, 2.7.10$^{-3}$ mole), corresponding to a EO/Li$^+$ ratio of approximately 20. The solution was stirred for another 8 hours, filtered and cast on a glass plate. After the evaporation of the solvent the resulting polymer membrane (thickness approx. 0.25 mm) was dried at high vacuum. The complex was purple and the conductivity was found to be 1.9.10$^{-6}$ S cm$^{-1}$ at room temperature.

EXAMPLE 4

The synthesis of:

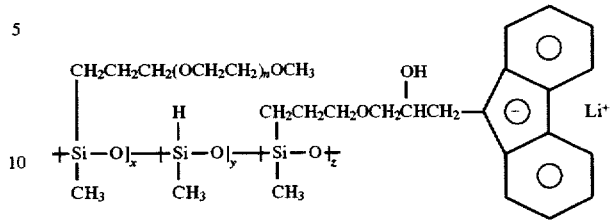

A tetrahydrofuran solution (40 ml) of polymethyl hydrosiloxane (1.35 g, 5.9.10$^{-4}$ mole (PS 120)), polyethyleneglycol allyl methyl diether (2.84 g, 7.3.10$^{-3}$ mole (MW=391)) and allyl glycidyl ether (0.36 g, 3.2.10$^{-3}$ mole) was placed in a 50 ml Erlenmeyer flask. The reaction was catalyzed by adding 7.5 µl platinum divinyl tetramethyldisiloxan complex [2]. The mixture was stirred for 20 hours followed by addition of lithium fluorenylide (0.45 g, 2.6.10$^{-3}$ mole (9-lithiumfluorene)), corresponding to a EO/Li$^+$ ratio of approximately 20. The solution was stirred for another 7 hours, filtered and then cast on a glass plate. After evaporation of the solvent the resulting polymer was a viscosious purple liquid.

Complexes made as described above, containing mixed salt mixtures of lithium cyclopentadienylide (example 1) and lithium fluorenylide, were solid complexes. The result of conductivity measurements of complexes containing 20–80 mole % (of total salt content) lithium fluorenylide (LiFl) is shown on the following table. The conductivity is obviously decreasing with increasing lithium fluorene content.

| % LiFl | Conductivity (S cm$^{-1}$) |
|---|---|
| 20 | 1.0 · 10$^{-6}$ |
| 60 | 7.4 · 10$^{-7}$ |
| 80 | 4.7 · 10$^{-7}$ |

EXAMPLE 5

The synthesis of

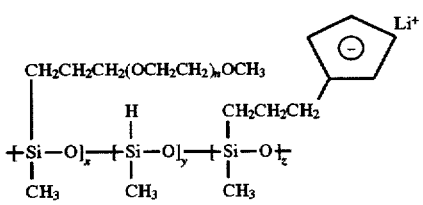

9.5 g polymethyl hydrosiloxane (4.2.10$^{-3}$ mole (PS 120)) and 20.1 g polyethyleneglycol allyl methyl diether (4.8.10$^{-2}$ mole (MW=415)) was dissolved in approximately 70 ml tetrahydrofuran in a 100 ml volumetric flask. A reaction between the components was catalyzed by adding 25 µl platinum divinyl tetramethyldisiloxan complex to the solution with a microsyringe[2]. The mixture was stirred for 5 hours and then diluted to 100.0 ml. (PMHS/PEG-matrix solution)

A polymer membrane with a EO/Li$^+$ ratio of approximately 10 was prepared as follows: 15.0 ml of the PMHS/PEG-matrix solution was placed in a 50 ml Erlenmayer flask followed by addition of $5.7 \cdot 10^{-3}$ mole of lithiumallylcyclopentadienylide dissolved in 7 ml of tetrahydrofuran. The solution was diluted to approximately 30 ml, stirred for 15 hours, diluted again to approximately 40 ml, filtered and cast on a glass plate. After evaporation of the solvent the resulting polymer membrane (thickness approx. 0.25 mm) was dried at high vacuum. The complex was brown and waxy. The conductivity was found to be $2.7 \cdot 10^{-5}$ S cm$^{-1}$ at room temperature.

EXAMPLE 6

The synthesis of:

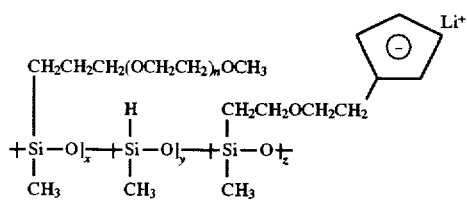

23.7 g polymethyl hydrosiloxane ($1.0 \cdot 10^{-2}$ mole (PS 120)) and 50.1 g polyethyleneglycol allyl methyl diether (0.121 mole (MW=415)) was dissolved in approximately 150 ml tetrahydrofuran in a 250 ml volumetric flask. A reaction between the components was catalyzed by adding 100 μl platinum divinyl tetramethyldisiloxan complex to the solution with a microsyringe[2]. The mixture was stirred for 15 hours and then diluted to 250.0 ml. (PMHS/PEG-matrix solution)

15.0 ml of the PMHS/PEG-matrix solution was placed in a 50 ml Erlenmeyer flask. The polymer was crosslinked by addition of 0.12 g polyethyleneglycol diallyl ether dissolved in 1.0 ml tetrahydrofuran ($4.4 \cdot 10^{-4}$ mole (MW=282)). After stirring for 4 hours, approximately $3.9 \cdot 10^{-3}$ mole of 2-(lithium cyclopentadienylide)ethyl-vinyl ether suspended in 8.3 ml tetrahydrofuran was added to the mixture, corresponding to a EO/Li$^+$ ratio close to 15. The solution was diluted to approximately 40 ml, stirred for 15 hours, filtered and cast on a glass plate. After evaporation of the solvent the resulting polymer membrane (thickness approx. 0.25 mm) was dried at high vacuum. The complex was brown and the conductivity was found to be $3.3 \cdot 10^{-6}$ S cm$^{-1}$ at room temperature.

EXAMPLE 7

The synthesis of:

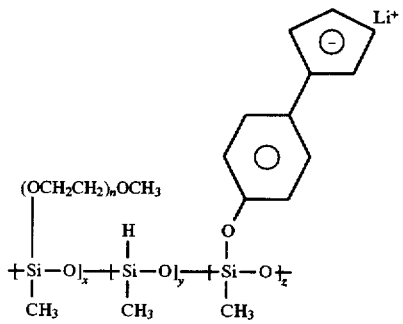

A 40 g sample of polymethyl hydrosiloxane ($1.8 \cdot 10^{-2}$ mole (PS 120)) was mixed with 70 g of polyethyleneglycol 350 monomethyl ether (0.20 mole) and 10 g phenol (0.11 mole). The mixture was dissolved in 300 ml tetrahydrofuran and placed in a 0.5 l three-necked flask. The reaction was catalyzed by adding 100 mg of zinc octoate to the solution[2] and the mixture was stirred at room temperature for 72 hours. The polymer was lithiated by addition of 40 ml N,N,N',N'-tetramethylethylenediamine (TMEDA) and 20 ml of 10M butyllithium solution[3,4,6]. The solution was refluxed overnight and then the solvent was removed a rotary evaporator. The resulting polymer (a yellow liquid) was washed three times with 100 ml of methylcyclohexane and dried at high vacuum (Yield 91.3 g (75%)).

A 26 g sample of the lithiated polymer was dissolved in 100 ml tetrahydrofuran. While the mixture was stirred and cooled in an ice bath, 2.5 ml of 2-cyclopentene-1-on was added[3]. The solution immediately became orange, but then slowly turned deep red while being stirred for 100 hours. The solvent was removed on a rotary evaporator whereby the polymer precipitated as beads.

3 g of the beads were suspended in 75 ml of tetrahydrofuran by stirring for 24 hours. Then they were treated with 0.25 ml of 10M butyllithium solution[3], corresponding to a EO/Li$^+$ ratio of approximately 20. The suspension was cast on a glass plate and after the evaporation of the solvent the resulting polymer membrane was dried at high vacuum. The conductivity of the complex was found to be $7.1 \cdot 10^{-6}$ S cm$^{-1}$ at room temperature.

EXAMPLE 8

The synthesis of:

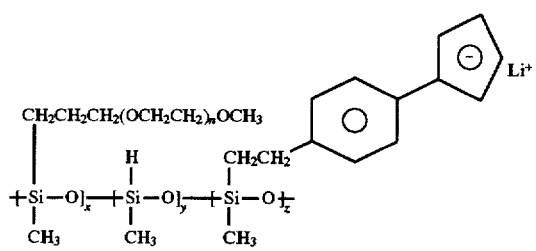

A 40 g sample of polymethyl hydrosiloxane ($1.8 \cdot 10^{-2}$ mole (PS 120)) was mixed with 78 g of polyethyleneglycol allyl methyl diether (0.20 mole (MW=391)) and 11 g freshly distilled styrene (0.11 mole). The mixture was dissolved in 300 ml tetrahydrofuran and placed in an 0.5 l three-necked flask. The reaction was catalyzed by adding 25 μl platinum divinyl tetramethyldisiloxan complex to the solution[2], and the mixture was stirred at room temperature for 72 hours. The polymer was lithiated by addition of 40 ml TMEDA and 20 ml of 10M butyllithium solution[3,4,6]. The solution was refluxed overnight and then the solvent was removed by a rotary evaporator. The resulting polymer (a orange liquid) was washed three times with 100 ml of methylcyclohexane and dried at high vacuum. (Yield 109.9 g (82%)).

A 28 g sample of the lithiated polymer was dissolved in 100 ml tetrahydrofuran. While the mixture was stirred and cooled in an ice bath, 2.5 ml of 2-cyclopentene-1-on was added[3]. The solution immediately became red, but then slowly turned brown while being stirred for 100 hours. The solvent was removed on a rotary evaporator whereby the polymer precipitated as beads.

4 g of the beads were suspended in 75 ml of tetrahydrofuran by stirring for 24 hours. Then they were treated with 0.30 ml of 10M butyllithium solution[3], corresponding to a EO/Li$^+$ ratio of approximately 20. The suspension was cast on a glass plate, and after the evaporation of the solvent the resulting polymer membrane was dried at high vacuum. The

EXAMPLE 9

The synthesis of:

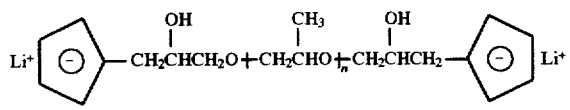

1.04 g (1.4.10$^{-2}$ mole) lithium cyclopentadienylide was weighed in a 100 ml volumetric flask and dissolved in approximately 50 ml tetrahydrofuran, followed by addition of 4.87 g (7.6.10$^{-3}$ mole) poly(propylene oxide)diglycidyl ether. The mixture was stirred for 24 hours and then diluted to 100.0 ml. (PPO solution)

A solution containing 0.74 g of polymethyl hydrosiloxane (3.3.10$^{-4}$ mole (PS 120)), 2.70 g polyethyleneglycol allyl methyl diether (4.6.10$^{-3}$ mole (Mw=591)) and allyl glycidyl ether (0.13 g, 1.1.10$^{-3}$ mole) in tetrahydrofuran was prepared in a 50 ml Erlenmeyer flask. A reaction between the existing carbon-carbon double bonds and the silicon-hydrogen bonds was catalyzed by adding 5.0 µl platinum divinyl tetramethyldisiloxan complex to the solution with a microsyringe[2]. The mixture was stirred for 15 hours followed by addition of 24 ml of the PPO solution, corresponding to a EO/Li$^+$ ratio of approximately 20. The solution was stirred for another 8 hours and cast on a glass plate. After evaporation of the solvent the resulting polymer membrane (thickness approx. 0.25 mm) was dried at high vacuum. The complex was red and seemed to be separated into two phases. The conductivity of the dominant phase was found to be 5.4.10$^{-6}$ S cm$^{-1}$ at room temperature.

EXAMPLE 10

The synthesis of:

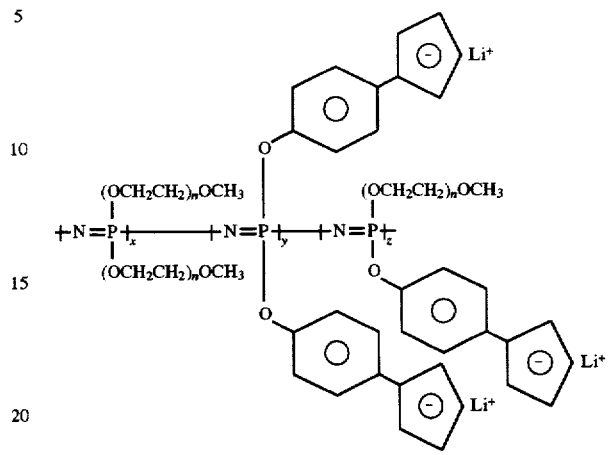

may be carried out in the following manner: A 12.5 g sample of phosphornitrile chloride (Cl$_2$N$_3$P$_3$) is polymerized by a ring opening polymerization at 250° C.[7]. The resulting polydichlorophosphazene is dissolved in 300 ml tetrahydrofuran and is added over a 0.5 hour period to a stirred suspension of 27.4 g of the sodium salt of triethyleneglycol monomethyl ether (polyoxyethylene-3-methylether (0.15 mole)) and 0.53 g of the disodium salt of polyethylene glycol 200 (2.1.10$^{-3}$ mole) in 200 ml tetrahydrofuran in a 1.0 l three-necked flask. The reaction is carried out in the presence of tetra-n-butyl ammonium bromide to yield a fully substituted polymer[8]. The mixture is refluxed for another 24 hours and then 7.7 g of the sodium salt of the phenol suspended in 100 ml tetrahydrofuran is added. The mixture is refluxed for another 24 hours and is then cooled to room temperature. The polymer is recovered by precipitation into heptane.

The resulting polymer is then lithiated, grafted with cyclopentadiene and complexed in the same manner as described in examples 7 and 8.

EXAMPLE 11

The synthesis of:

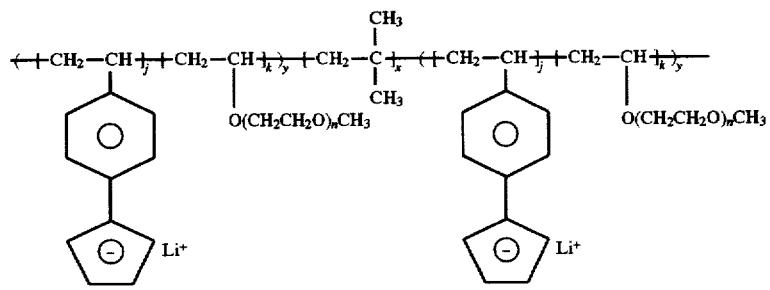

may be carried out in the following manner: A polymer of the PVE-type, polyalkane, polystyrene or a combination thereof in a random copolymer or block-copolymer is prepared by living carbocationic polymerization with 1,3-di-(2-methoxy-2-propyl)-5-tert-butylbenzene as an initiator, with titanium$^{(IV)}$ chloride as coinitiator. An ideal solvent system may be a 40:60 (v/v) mixture of methylcyclohexane and dichloromethane[12,13,14]. The polymerization is carried out at −78° C., in a cooling bath consisting of isopropyl alcohol mixed with dry ice. A proton trap such as 2,6-di-tert-butyl-pyridine and an electron donor such as DMA may optionally be applied. The resulting polymer is rinsed for homopolymers by soxhlet extraction with ethyl methyl ketone as an eluent. The apparent average molecular weight of the purified polymer may be measured by Gel Permeation Chromatography (GPC) with polyisobutylene, polystyrene and/or poly(ethylene glycol) standards, depending on the actual composition[12,13,14].

A block-copolymer consisting of a middle-block of polyisobutylene and random end-blocks of polystyrene-co-poly-(ethylene glycol) methyl vinyl diether is prepared by living carbocationic polymerization in the said system, by preparing a solution of the initiator, proton trap, and isobutylene according to the art. The polymerization is turned on by adding a solution of the coinitiator to the system. After a while (typically 1–5 hours) the electron donor is added, followed by addition of a solution of poly(ethylene glycol) methyl vinyl diether and styrene. The polymerization is quenched with methanol after another 2–3 hours[12,14].

The polymer is the lithiated, grafted with cyclopentadiene and complexed in the same manner as described in examples 7 and 8.

EXAMPLE 12

The synthesis of:

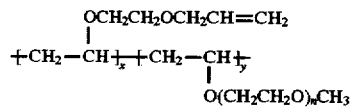

may be carried out in the following manner: A random copolymer of poly(ethylene glycol) methyl vinyl diether and ethylene glycol allyl diether (allylated PVE)[15,16] is prepared by living carbocationic polymerization, in the same system as described in example 11, by preparing a solution of the initiator, proton trap, and the said monomers according to the art. The polymerization is turned on by adding a solution of the coinitiator to the system. After typically 1–5 hours, the polymerization is quenched with methanol[12,13,14].

The ion-conductivity may be gained by mixing the resulting copolymer with a polymer containing an ion complex of the invention, such as a poly(methyl hydrosiloxane) derivative (examples 1 and 2). In this case a crosslinking reaction occurs between the Si—H bond in the poly(methyl hydrosiloxane) and the double bond in the allylated PVE.

EXAMPLE 13

The synthesis of:

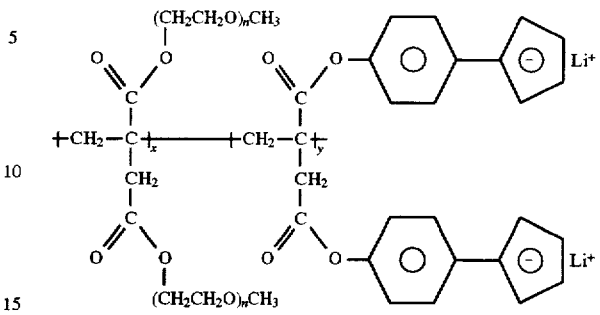

may be carried out in the following manner: Itaconate ester monomers may be prepared by acid catalyzed esterification of itaconic acid with the appropriate starting alcohol using p-toluene sulfonic acid as catalyst and toluene as solvent at reflux temperature. Alcohols such as polyethylene glycol 350 monomethyl ether, triethylene glycol monomethyl ether and phenol, may be used for the monomer synthesis. The corresponding itaconates are di-ethoxy(7,2)-methyl itaconate, di-ethoxy(3)-methyl itaconate and diphenyl itaconate. Unreacted alcohol is removed by washing the toluene solution several times with water. The required monomer may then be obtained by drying the toluene solution with magnesium sulphate, followed by azeotropic distillation[17,18,19,20].

A mixture of di-ethoxy(7,2)-methyl itaconate, di-ethoxy(3)-methyl itaconate and diphenyl itaconate is placed in a 0.5 l flask. The monomers are polymerized using α,α'-azabisisobutyronitrile as initiator by heating the system at 340 K for one week. The resulting polymer is dissolved in chloroform, precipitated from diethyl ether and dried for 24 hours in vacuo[17,18,19,20].

The polymer may then be lithiated, grafted with cyclopentadiene and complexed in the same manner as described in examples 7 and 8, with carefully purified and dried dichloromethane as solvent.

In the case of y=0, ion-conductivity may be gained by mixing the resulting poly(poly(ethylene glycol) monomethyl ether) itaconate with a polymer containing an ion complex of the invention, such as a poly(methyl hydrosiloxane) derivative (example 1 and 2).

REFERENCES

1 Gray, F. M.: "Solid Polymer Electrolytes-Fundamentals and Technological Applications", VHC Publishers Inc. 1991.

2 Anderson, R., Arkles, B., and Larson, G. L.: "Silicon Compounds-Register and Review", Petrarch Systems Inc. 1987.

3 Bonds, W. D., Brubaker, Jr., C. H., Chandrasekaran, E. S., Gibbons, R. H. and Kroll, L. C.: "Polystyrene Attached Titanocene Species-Preparation and Reactions", J. Am. Chem. Soc. 97(8), 2128 (1975).

4 Fyles, T. M. and Leznoff, C. C.: "The Use of Polymer Supports in Organic Chemistry V. The Preparation of Monoacetates of Symmetrical Diols", Can. J. Chem. 54, 935 (1976).

5 Grubbs, R. H. and Shiu.Chin, H. Su: "The Preparation of Polymeric Organophosphorous Ligands for Catalyst Attachment", J. Organom. Chem. 122, 151 (1976).

6 Broaddus, C. D.: "Homogenous Metalation of Alkylbenzenes", J. Org. Chem. 35, 10 (1970).

7 Allcock, H. R., Austin, P. E., Neenen, T. X., Sisko, J. T., Blonsky, P. M. and Shriver, D. F.: "Polyphosphazenes with Etheric Side Groups: Prospective Biomedical and Solid Electrolyte Polymers", Macromolecules 19, 1508 (1986).

8 Blonsky, J. T. and Shriver, D. F: "Polyphosphazenes Solid Electrolytes", J. Am. Chem. Soc. 106, 6854 (1986).

9 Tonge, J. S. and Shriver, D. F.: "Increased Dimensional Stability in Ionically Conducting Polyphosphanozenes systems", J. Electrochem. Soc. 134, 269 (1984).

10 Feldstedt, J.: "Syntese og Karakterisering af Solventfrie Elektrolytter", DTH Kemisk Lab. A, Denmark 1991.

11 Skotheim, T. A., Yoshiyuki, O. and Hung Sui, L.: European Patent Application Publ. No. 0376466.

12 Kennedy, J. P. and Iván, B.: "Designed Polymers by Carbocationic Macromolecular Engineering: Theory and Practice.", Hanser Publichers, 1992.

13 Wang, B., Mishra, M. K. and Kennedy, J. P.: "Living Carbocationic Polymerization. XII. Telechelic Polyisobutylenes by a Sterically Hindered Bifunctional Initiator.", Polymer Bulletin 17, 205, (1987), Springer-Verlag 1987.

14 Gylfason, G. H.: "Polymerer med kontrolleret struktur", DTH Institut for kemiteknik. 1993.

15 Andrei, M., Marchese M. and Roggero A.: "Polymer Electrolytes Based on Crosslinked Siliated Poly-vinylether and Lithium Perchlorate.", Solid State Ionics 72, 140, (1994).

16 Pantaloni, S., Passerini, S., Croce, F. and Scrosati B.: "Electrochemical Characterization of a Class of Low Temperature Conducting Polymer Electrolytes.", Electrochimica Acta 34/5, 635, (1989).

17 Cowie, J. M. G., Ferguson, R.: "Glass and Subglass Transitions in a Series of Poly(itaconate ester)s with Methyl-Terminated Poly(ethylene oxide) Side Chains.", J. Polymer Science, Polymer Physics Ed. 23, 2181, (1985).

18 Cowie, J. M. G. and Martin, A. C. S.: "Ionic Conductivity of Poly(diethoxy(3)methyl itaconate) Containing Lithium Perchlorate.", Polymer Communications 26, 298, (1985).

19 Cowie, J. M. G. and Martin, A. C. S.: "Glass Transition in Poly(di-(polypropylene glycol)itaconate)-Salt Mixtures.", Polymer Communications 28, 130, (1987).

20 Cowie, J. M. G. and Martin, A. C. S.: "Ionic Conductivity of Poly(di-(polypropylene glycol)itaconate)-Salt Mixtures.", Polymers 28, 627, (1987).

We claim:

1. An ion-conductive polymer containing covalently bound ion complexes of one of the formulas Ia–Ic

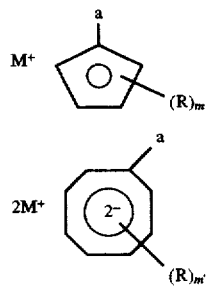

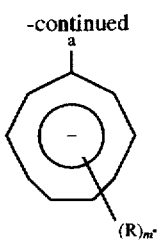

wherein $M^+$ is $H^+$, $Li^+$, $Na^+$, or $K^+$;

m is an integer in the range 0–4;

m' is an integer in the range 0–7;

m" is an integer in the range 0–8; and each group R independently is halogen;

a group —CO—O$^-$, —CO—O$^-$M$^+$, or —SO$_2$—O$^-$, M$^+$ wherein M$^+$ is as defined above;

cyano;

nitro;

$C_{1-5}$ alkoxy;

optionally substituted phenyl;

optionally substituted phenoxy;

a group —CONR$^5$R$^6$ where R$^5$ and R$^6$ independently are hydrogen, $C_{1-5}$ alkyl, optionally substituted phenyl, phenylcarbonyl, or $C_{1-6}$ alkanoyl;

a group —NR$^5$R$^6$ where R$^5$ and R$^6$ independently are as defined above;

a group —N(R$^5$)—CO—R$^7$ where R$^5$ is as defined above, and R$^7$ is hydrogen, $C_{1-5}$ alkyl, $C_{2-5}$ alkenyl, $C_{2-5}$ alkynyl, or optionally substituted phenyl; a group R$^7$—CO—, a group R$^7$—O—CO—, a group R$^7$—CO—O—, or a group R$^7$—O—CO—O, where R$^7$ is as defined above; cycloheptatrienyl; or one of the groups R is a ion complex Ia', Ib', or Ic'

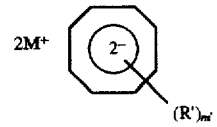

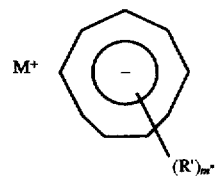

wherein M$^+$, m, m' and m" are defined above, and R' has the same meanings as R defined above with the proviso that R' is not a ion complex Ia', Ib', or Ic'; or two groups R bound to two adjacent carbon atoms may together form a divalent aliphatic or alicyclic group with 3–8 carbon atoms and having at least 2 C—C double bonds;

carbonyloxycarbonyl;

carbonylthiocarbonyl;

a group —CO—N(R$^7$)—CO— where R$^7$ is as defined above;

and the free bond indicated by "a", either directly or through an intervening group, is bound to the polymer backbone.

2. A polymer according to claim 1 in which a divalent aliphatic or alicyclic group formed by two groups R bound to two adjacent carbon atoms is selected from 1,3-propenylene, 1- or 2-buten-1,4-ylene, 1,3-butadien-1,4-ylene, 1,3-pentadien-1,5-ylene, 5-methyl-1,3-pentadien-1,5-ylene, 3-methyl-1,4-pentadien-1,5-ylene, 5-methylidene-1,3-pentadien-1,5-ylene, a group of the formula

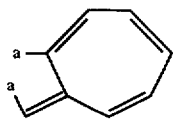

and a group of the formula

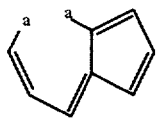

where "a" indicate the free bonds to two adjacent carbon atoms.

3. A polymer as claimed in claim 1 which has a glass transition temperature $T_g$ is below 273° K.

4. A polymer as claimed in claim 3 where the glass transition temperature $T_g$ is below 263° K.

5. A polymer as claimed in claim 4 where the glass transition temperature $T_g$ is below 253° K.

6. A polymer as claimed in claim 5 where the glass transition temperature $T_g$ is below 243° K.

7. A polymer as claimed in claim 6 where the glass transition temperature $T_g$ is below 233° K.

8. A polymer as claimed in claim 7 where the glass transition temperature $T_g$ is below 223° K.

9. A polymer as claimed in claim 1 which further comprises sequences of the formula —(CH(Y)—CH$_2$—O)$_n$— where n is an integer in the range of 2–30, and each Y independently is hydrogen or methyl, said sequences being present either in the backbone of the polymer or in grafted side groups or in the intervening group.

10. A polymer as claimed in claim 9 in which n is in the range of 3–10.

11. A polymer as claimed in claim 9 wherein the intervening group or grafted side groups comprise sequences of the formula —(CH(Y)—CH$_2$—O)$_n$—.

12. A polymer as claimed in claim 1 which comprises a backbone derived from polymer backbones of the following formulae II, III or IV

wherein X is halogen;

$R^{10}$ and $R^{11}$ independently are hydrogen, alkyl with 1–3 carbon atoms, carboxy, carboxyalkyl with 1–3 carbon atoms, phenyl, a group —(OCH(Y)CH$_2$)$_n$OH or a group —(OCH(Y)CH$_2$)$_n$OR$^{12}$ wherein Y is H or methyl, n is an integer in the range 2–30 and R$^{12}$ is C$_{1-3}$ alkyl; and y is an integer in the range from 3 to 10$^4$.

13. A polymer as claimed in claim 12 in which y is in the range from 3 to 10$^3$.

14. A polymer as claimed in claim 13 in which y is in the range from 3 to 500.

15. A polymer as claimed in claim 1 where M$^+$ is H$^+$; m, m' and m" are different from 0; the polymer contains sequences of the formula —(CH(Y)—CH$_2$—O)$_n$— where Y is hydrogen or methyl, and n is an integer in the range of 2–30; the ion complex of formula Ia, Ib, or Ic further having a pK$_a$ value of at the most 15.

16. A polymer as claimed in claim 15 wherein pK$_a$ value of the ion complex is at the most 10.

17. A polymer as claimed in claim 16 wherein pK$_a$ value of the ion complex is at the most 5.

18. A polymer as claimed in claim 17 wherein pK$_a$ value of the ion complex is at the most 0.

19. An electrochemical battery comprising an electrolyte comprising a polymer as defined in claim 1.

20. A proton exchange membrane fuel cell comprising an electrolyte comprising a polymer as defined in claim 1 wherein M$^+$ is H$^+$.

* * * * *